United States Patent [19]

Adinolfi

[11] Patent Number: 5,109,842
[45] Date of Patent: May 5, 1992

[54] IMPLANTABLE TACHYARRHYTHMIA CONTROL SYSTEM HAVING A PATCH ELECTRODE WITH AN INTEGRATED CARDIAC ACTIVITY SYSTEM

[75] Inventor: David W. Adinolfi, Santa Clarita, Calif.

[73] Assignee: Siemens Pacesetter, Inc., Sylmar, Calif.

[21] Appl. No.: 587,282

[22] Filed: Sep. 24, 1990

[51] Int. Cl.$^5$ .............................................. A61N 1/39
[52] U.S. Cl. ............................. 128/419 D; 128/642; 128/784
[58] Field of Search ............... 128/419 P, 419 D, 642, 128/784

[56] References Cited

U.S. PATENT DOCUMENTS

3,815,611  6/1974  Denniston, III ................. 128/419 D
4,314,095  2/1982  Moore et al. ........................ 128/642

Primary Examiner—William E. Kamm
Assistant Examiner—Scott M. Getzow
Attorney, Agent, or Firm—Leslie S. Miller; Lisa P. Weinberg

[57] ABSTRACT

An implantable tachyarrhythmia control system includes a patch electrode having a sensor integrated therein, such as a piezoelectric sensor, which is capable of monitoring mechanical heart activity. When the patch electrode is sutured to the cardiac tissue, the piezoelectric sensor will be deformed due to the mechanical activity of the heart muscle, and will generate a corresponding electrical signal. The electrical signal from the sensor will exhibit relatively low-frequency periodicity and relatively low amplitude during normal heart activity. In the event of tachycardia or fibrillation, the signal will exhibit excursions beyond those occurring for normal heart activity, and will consequently have a higher energy content. The signal is thus an indicator for the onset of these cardiac events. The signal can be supplied to an implantable defibrillator and can be used as a primary or secondary trigger for initiating defibrillation therapy, such as one or more defibrillating pulses. The signal may alternatively be supplied to an implantable combination pacemaker/-defibrillator, which also undertakes standard R-wave detection via a conventional pacing lead. The signal from the patch electrode sensor can be used as before as a primary or secondary trigger to initiate defibrillation therapy alone or in combination with the detected R-wave signal. The patch sensor signal may also be used, alone or in combination with the R-wave signal, to initiate a change in the pacing mode or to initiate a particular pacing therapy, such as an antitachycardia sequence.

37 Claims, 5 Drawing Sheets

IMPLANTABLE TACHYARRHYTHMIA CONTROL SYSTEM HAVING A PATCH ELECTRODE WITH AN INTEGRATED CARDIAC ACTIVITY SYSTEM

BACKGROUND OF THE INVENTION

1. Field of the Invention

The present invention relates to cardiac defibrillating and pacing systems, and in particular to implantable systems of this type employing a patch electrode.

2. Description of the Prior Art

Many types of implantable systems are known for tachyarrhythmia control. Such systems have gained greater acceptance in recent years as an alternative therapy to chronic pharmacologic treatment. Such tachyarrhythmia control systems typically include an implantable device capable of tachyarrhythmia detection and delivery of an automatic therapeutic response to the arrhythmia, including bradycardia pacing support, anti-tachyarrhythmia pacing, low energy synchronized cardioversion or high energy defibrillation shock, an electrode system for sensing and pacing, and a high energy electrode system for delivery of defibrillation shock. Typically the pacing and sensing electrode system will consist of a bipolar endocardial lead or two unipolar myocardial leads. The high energy electrode system generally consists of two myocardial patches or a transvenous shocking electrode and a myocardial or subcutaneous patch.

Any device which is intended to provide automatic treatment of ventricular tachyarrhythmias must be capable of first detecting the presence of such arrhythmias prior to the onset of therapy. Several methods are known for detecting ventricular tachyarrhythmias. These include monitoring an absolute heart rate interval, and initiating therapy when the interval becomes less than a programmable interval threshold. It is also known to try to differentiate pathologic rhythms from normal physiologic rhythms by analyzing the rate of onset (sudden change, as opposed to gradual change in the heart rate interval) and/or heart rate stability. It is also known to determine the probability density function of a signal corresponding to heart activity, which involves the evaluation of the time which the cardiac electrical signal spends at an isoelectric base line, and to initiate therapy when deviations beyond a predetermined threshold occur.

The known detection techniques have several limitations and disadvantages. The two major disadvantages are (1) no accurate method of differentiating between a pathologic (i.e. hemodynamically compromising) rhythm versus a physiologic (i.e., sinus) rhythm, and (2) total reliance on a processed electrogram for detection of cardiac depolarization. As a result of the second disadvantage, certain rhythms, particularly low amplitude ventricular fibrillation, may not be detected. These limitations in the known detection techniques may result either in a false positive detection response (inappropriate shock delivery) or a false negative detection response (failure to respond to a pathologic rhythm).

SUMMARY OF THE INVENTION

In accordance with the principles of the present invention, a tachyarrhythmia control system is provided with a patch electrode having a motion sensor, such as a piezoelectric sensor, integrated in the patch electrode. The patch electrode is otherwise of the type conventionally used for delivery of high energy defibrillating shock. The patch electrode is attached to cardiac tissue, such as by placement directly on the myocardial surface, or the pericardial sac, so that wall motion of the cardiac muscle can be evaluated. Activity of the cardiac muscle deforms the piezoelectric sensor, thereby causing an electrical signal to be generated corresponding to the cardiac motion. The output of the sensor is processed and is monitored by the implantable device to determine the extent of the wall motion, the cardiac energy, and/or the frequency of myocardial motion to determine and differentiate the specific myocardial rhythm of an individual patient. The sensor can be used as a primary or secondary indicator of the onset of ventricular tachyarrhythmias, including ventricular fibrillation in a conventional implantable defibrillating system, or can be used in combination with a conventional R-wave detection system in a combination defibrillating and pacing system. In the latter system, the signal from the sensor can be used, alone or in combination with the R-wave signal, as a primary or secondary indicator of tachycardia, and can thus trigger the initiation of an antitachycardia pacing mode, low energy cardioversion or defibrillation, or such other pacing modes as may be responsive to the pathology indicated by the sensor signal.

The system disclosed herein permits a nonelectrogram-dependent means of either primary detection and differentiation of a pathologic versus physiologic cardiac rhythm, or as a secondary decision point of confirmation in the treatment algorithm for the selection of a particular therapy. The system embodying the motion sensor can be used in combination with conventional electrogram detection methods described above, and can be programmable by a physician to allow selection by the physician of use of the sensor signal alone as a therapy-determining indicator, or use of the sensor signal in combination with other detected signals.

The system operates based on the knowledge that in a normal physiologic cardiac rhythm, electrical depolarization and subsequent myocardial wall motion follows a specific pattern and sequence, and that an effective myocardial systole will result in a recognizable, identifiable myocardial excursion and energy. A pathologic (hemodynamically compromising) cardiac rhythm, by contrast, will result in an ineffective and/or chaotic cardiac wall motion. Monitoring of the excursion of the cardiac wall and the energy associated with the sensor signal permits discrimination between pathologic and physiologic rhythms.

During testing of the system at the time of implantation, various cardiac rhythms can be deliberately induced and the output of the sensor can be recorded and stored during these rhythms, for use as a template for comparison purposes during actual clinical use following implantation.

DESCRIPTION OF THE DRAWINGS

The advantages of the present invention are best understood with reference to the drawings, in which.

DESCRIPTION OF THE PREFERRED EMBODIMENTS

Figure 1:
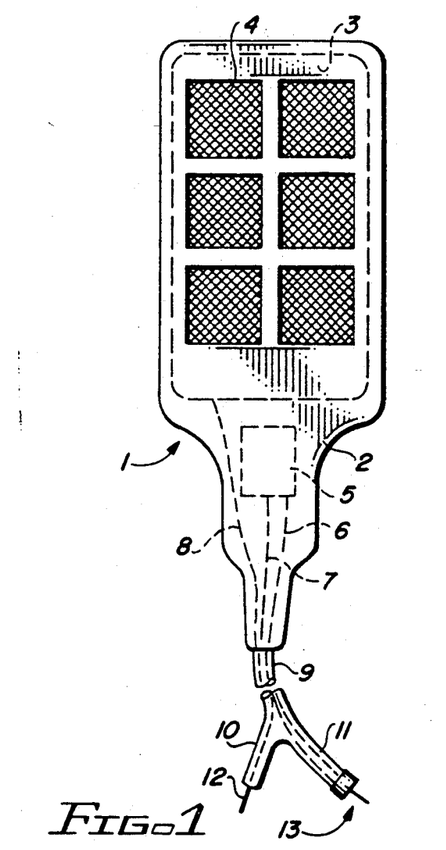
FIG. 1 is a plan view of a first embodiment of a patch electrode having a two-terminal lead for use in an implantable tachyarrhythmia control system constructed in accordance with the principles of the present invention.

A patch electrode 1 constructed in accordance with the principles of the present invention is shown in FIG. 1. The electrode consists of a carrier 2 consisting of Dacron ®—reinforced silicone sheeting. The surface of the patch electrode 1 which is intended for contact with the myocardium is visible in FIG. 1. The opposite side of the patch electrode 1 is completely covered by the silicone sheeting. Embedded within the carrier 2 is a wire mesh 3, such as a titanium mesh, which is electrically conductive. The carrier 2 has a number of windows or openings 4 on the side thereof intended for contact with the myocardium. The mesh 3 is directly exposed to the myocardium through these openings.

Also embedded within the carrier 2 is a motion sensor 5, such as a piezoelectric sensor. The carrier 2 is sufficiently flexible so that when the carrier 2 is sutured to the myocardium, or to the pericardial sac, the motion sensor 5 will mechanically interact with the cardiac tissue and will generate an electrical signal corresponding to the mechanical activity of the cardiac tissue. Specifically, the wall motion of the cardiac muscle will deform the carrier 2, and the motion sensor 5 embedded therein. It will be understood that the outline indicating the motion sensor 5 is for schematic representation only, and the actual extent and size of the motion sensor may be varied as needed. In general, however, the motion sensor 5 will preferably be disposed in the neck of the patch electrode 1, where the carrier 2 begins to taper for the cable which leads to the remainder of the implantable system. Alternately, the motion sensor 5 could be located on the main portion of the patch electrode 1.

Figure 11:
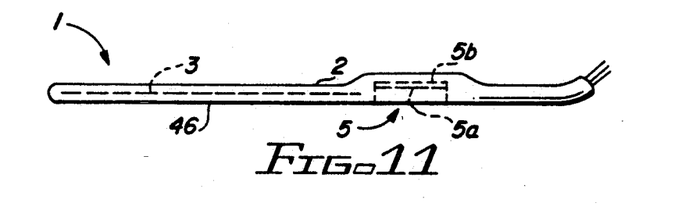
FIG. 11 is a side view of a patch electrode constructed in accordance with the principles of the present invention showing a first location for placement of the motion sensor.
Figure 12:
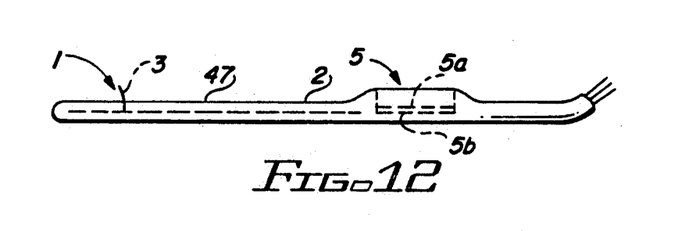
FIG. 12 is a side view of a patch electrode constructed in accordance with the principles of the present invention showing a second location for placement of the motion sensor.

As also shown in FIG. 1, the motion sensor 5 has leads 6 and 7 associated therewith, which are conducted via an insulated cable 9 to a distal end of the patch electrode. The wire mesh 3 also has a lead 8 extending therefrom, which is also conducted via the cable 9 to the distal end of the electrode. In the embodiment of FIG. 1, the distal end of the electrode is divided into a branch 10, with a terminal 12, for the wire mesh lead 8, and a branch 11 with a terminal assembly 13 for the motion sensor leads. The cable 9 may be a Teflon ® coated cable with the leads being drawn-brazed-stranded (DBS) wire. The motion sensor 5 may be formed by a piezoelectric crystal 5a mounted on a metallic backing 5b, such as a titanium strip, as schematically shown in FIGS. 11 and 12. Standard connectors may be used as the terminals 12 and 13.

Figure 2:
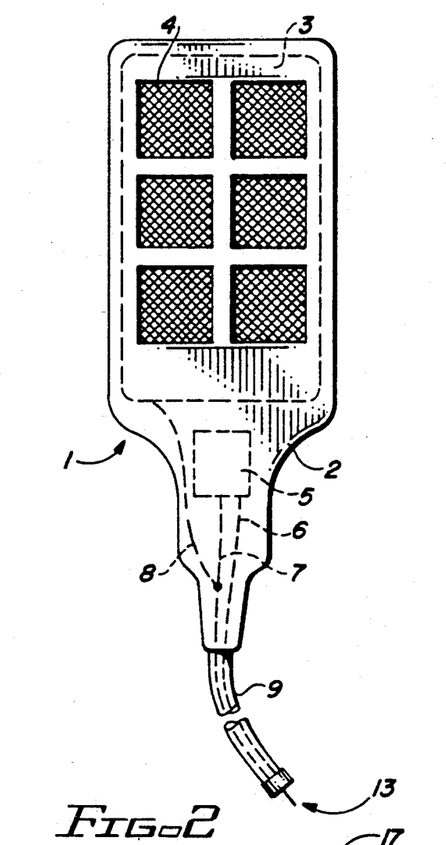
FIG. 2 is a plan view of a second embodiment of a patch electrode having a single terminal lead for use in an implantable tachyarrhythmia control system constructed in accordance with the principles of the present invention.

A second embodiment of a rectangular patch electrode I is shown in FIG. 2, wherein components identical to those shown in FIG. 1 have been provided with the same reference numerals. In the embodiment of FIG. 2, the cable 9 is not branched, and terminates in a single terminal assembly 13. In order to avoid the branching and the dual terminals of the embodiment of FIG. 1, the embodiment of FIG. 2 uses the lead 8 from the wire mesh 3 as one of the cable leads for the motion sensor 5. To this end, one of the leads from the motion sensor 5, such as the lead 7, is connected to the lead 8 within the carrier 2.

As shown in FIG. 11, the motion sensor 5 may be placed adjacent to a surface 46 of the carrier 2 which is intended for contact with the myocardium, or as shown in FIG. 12 may be placed adjacent a surface 47 of the carrier 2 which is intended to face away from the myocardium when the patch electrode 1 is in place. As can also be seen in FIGS. 11 and 12, the neck portion of the patch electrode 1 which forms the transition to the cable is slightly thicker than the remainder of the patch electrode 1. The carrier 2 is still sufficiently flexible at this location to permit the motion sensor 5 to flex in response to cardiac wall movement, however, placement of the motion sensor 5 at this thicker portion of the electrode affords protection against severe bending of the motion sensor 5, which could crack or otherwise damage the sensor.

The patch electrode is not limited to the rectangular configuration shown in the embodiments of FIGS. 1 and 2, but may be configured in any number of other shapes, examples of which are respectively shown in FIGS. 3 through 6. In each of these embodiments, only the location of the motion sensor 5 is schematically shown, with the other details being omitted. It will be understood that in each of the embodiments of FIGS. 3 through 6, either type of electrical connection as shown in FIGS. 1 and 2 can be used, and the motion sensor 5 can be placed at either of the locations shown in FIGS. 11 and 12.

Figure 3:
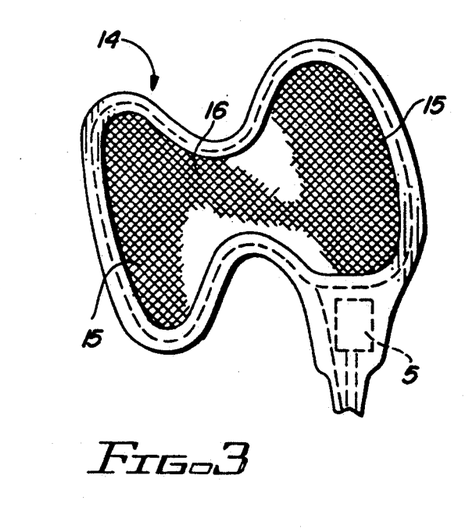
FIGS. 3 is a plan view of a further embodiment of a "butterfly" shaped patch electrode for use in an implantable tachyarrhythmia control system constructed in accordance with the principles of the present invention.

A patch electrode 14 is shown in FIG. 3 having a general "butterfly" or "figure-eight" shape with two generally elliptical regions 15 being joined by a narrow region 16. The connection to the cable lead, and the location of the motion sensor 5, are at a side of one of the regions 15 closest to the narrow region 16.

Figure 4:
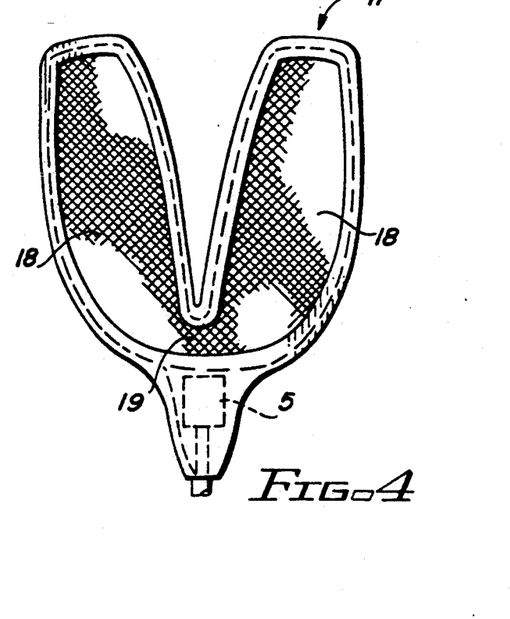
FIGS. 4 is a plan view of a further embodiment of a "rabbit ear" shaped patch electrode for use in an implantable tachyarrhythmia control system constructed in accordance with the principles of the present invention.

The embodiment of FIG. 4 shows a patch electrode 17 having a general "rabbit ear" shape consisting of two elongated lobes 18 joined by a narrow region 19. The attachment to the cable and the location of the motion sensor 5 are at a side of the electrode 17 close to the narrow region 19.

Figure 5:
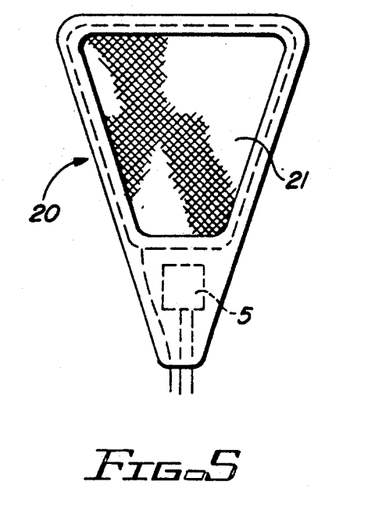
FIGS. 5 is a plan view of a further embodiment of a triangular shaped patch electrode for use in an implantable tachyarrhythmia control system constructed in accordance with the principles of the present invention.

A triangular patch electrode 20 is shown in FIG. 5 consisting of a single triangular electrode region 21. The cable connection and the motion sensor 5 are located at an apex of the triangle. In the embodiment of FIG. 5, the triangle is an isosceles triangle, and the apex at which the motion sensor 5 is located is the apex at which the two equal-length sides meet.

Figure 6:
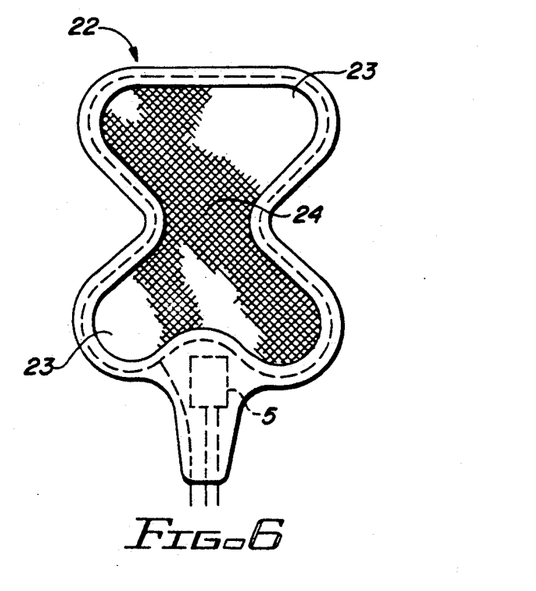
FIGS. 6 is a plan view of a further embodiment of a "figure-eight" shaped patch electrode for use in an implantable tachyarrhythmia control system constructed in accordance with the principles of the present invention.

The patch electrode 22 shown in FIG. 6 is a "butterfly" or "figure-eight" electrode similar to that shown in FIG. 3, consisting of two generally oval regions 23 separated by a narrower region 24. Differing from the embodiment of FIG. 3, the motion sensor 5 and the cable connection are located at a side of one of the lobes 23 farthest from the narrow region 24.

Figure 7:
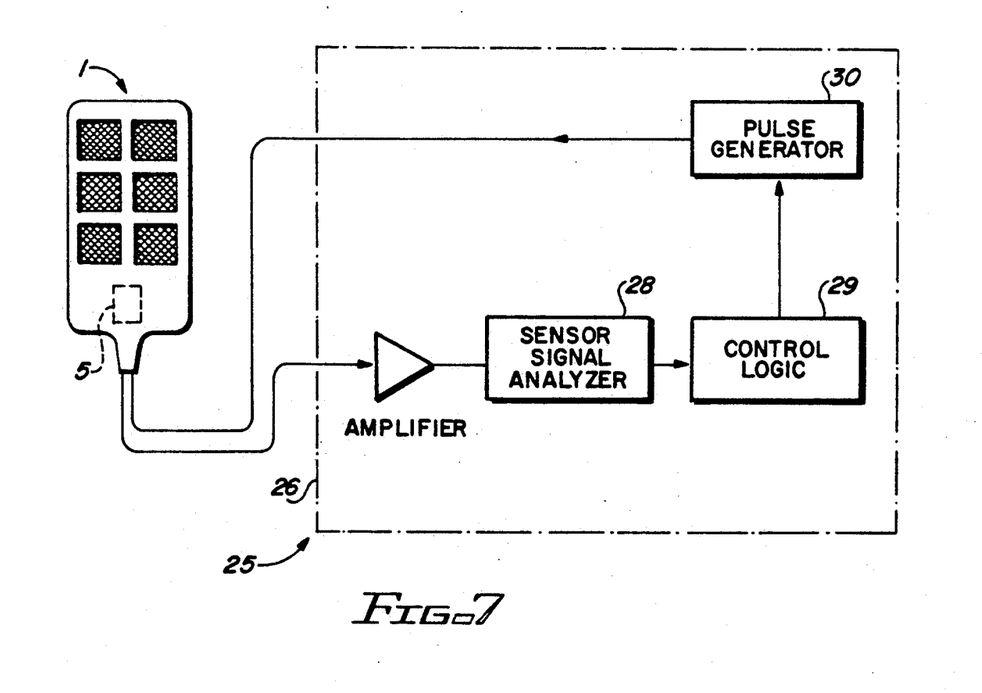
FIG. 7 is a schematic block diagram of an implantable defibrillator system constructed in accordance with the principles of the present invention using a single patch electrode.

An implantable defibrillator system 25 constructed in accordance with the principles of the present invention is schematically shown in FIG. 7. The system 25 consists of a patch electrode having a motion sensor 5 embedded therein, as described above, electrically connected to components within an implantable housing 26. The leads (schematically indicated as a single line) from the motion sensor 5 are electrically connected to an input of an amplifier 27. The amplified sensor signal from the output of the amplifier 27 is supplied to a sensor signal analyzer 28. As explained in more detail below, the sensor signal analyzer will examine one or more characteristics of the sensor signal, such as amplitude, frequency, energy content, etc., and will generate an output signal if one or a selected combination of these characteristics deviates from a standard or normal value by more than a predetermined threshold.

The chaotic cardiac wall motion, for example, which occurs during ventricular fibrillation will cause amplitude excursions of the motion sensor signal which dramatically exceed the amplitude which will be present during normal cardiac activity. This type of deviation will be identified within the sensor signal analyzer 28, and upon the detection of a characteristic, or set of characteristics, indicating abnormal cardiac activity, the sensor signal analyzer 28 will supply a signal to control logic 29. The control logic 29 may use the signal from the sensor signal analyzer 28 as a primary indicator of the onset of fibrillation or ventricular tachycardia, or may use the signal from the sensor signal analyzer 28 as a confirmation of the occurrence of fibrillation or ventricular tachycardia which has been detected by one of the aforementioned known techniques. In the event of an identification or confirmation of the onset of fibrillation or ventricular tachycardia based on the output of the sensor signal analyzer 28, the control logic 29 will enable a pulse generator 30 for generation of a high energy defibrillation pulse. This is delivered via the wire mesh electrode in the patch electrode 1.

In the embodiment of FIG. 7, a single patch electrode is shown, with the electrode preferably being sutured in the region of the ventricle of the heart, primarily for detecting ventricular defibrillation (but also capable of detecting tachycardia). A second patch electrode (not shown) could be placed on the opposite side of the heart. The second patch in this embodiment would not have a sensor mounted thereon. Alternately, a second electrode (not shown) could be transvenously placed within the heart, or close thereto.

Figure 8:
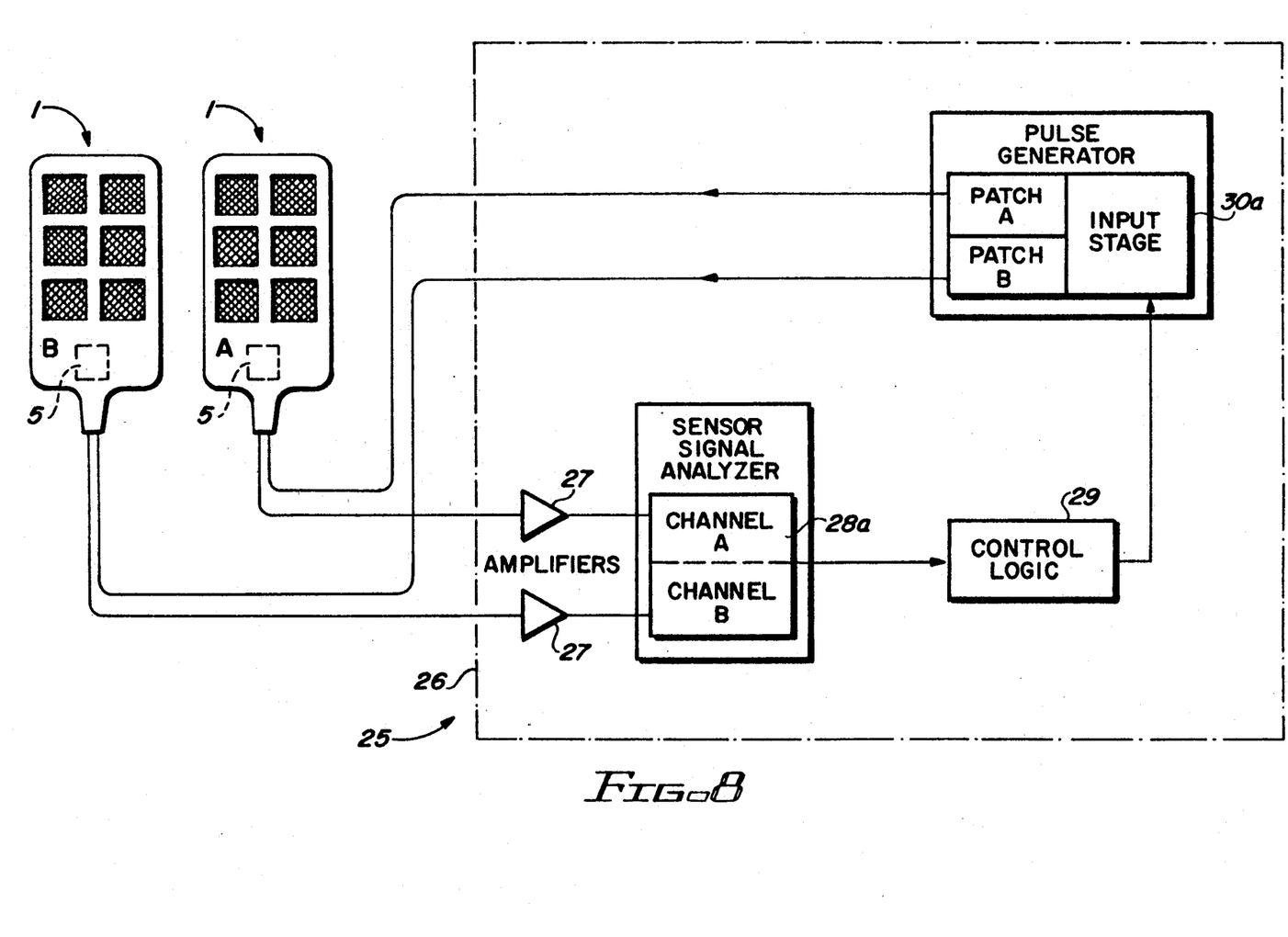
FIG. 8 is a schematic block diagram of an implantable defibrillator constructed in accordance with the principles of the present invention using two patch electrodes.

In the embodiment shown in FIG. 8, however, two patch electrodes 1, each having a motion sensor 5 embedded therein, are employed. These patch electrodes 1 will be respectively sutured to the front and back (or left and right) of the cardiac myocardium. This permits the location of abnormal cardiac wall activity to be more precisely isolated, so that different types of defibrillation or antitachycardia pacing therapy may be instituted. In the dual patch/piezo approach, one patch may be placed in the region of the right atrium to allow differentiation of atrial or ventricular arrhythmias, and also to allow determination of the relationship between atrial and ventricular activity to further discriminate a pathologic from physiologic disarrhythmia.

The defibrillation system 25a of FIG. 8 includes an implantable housing 26 having components therein to which the patch electrodes 1 are electrically connected. The respective leads (again schematically shown as a single line) from the motion sensors 5 are supplied to the respective inputs of amplifiers 27. In the embodiment of FIG. 8, a sensor signal analyzer 28a, having channel A for analyzing signals from one of the motion sensors 5, and a channel B for analyzing signals from the other motion sensor 5, is provided. The sensor signal analyzer 28a provides an output signal to the control logic 29 which not only identifies the occurrence of abnormalities as described above in connection with FIG. 7, but also identifies which channel, and thus from which patch electrode the abnormalities have been sensed. The sensor signal analyzer 28a may generate a signal on a single line leading to the control logic 29 which includes encoded information identifying the abnormalities in both channels, however, it will be understood that alternatively a separate line may be provided from each channel to the control logic 29.

In the event of the detection of an abnormality indicating the onset of fibrillation or ventricular tachycardia, the control logic 29 supplies an enabling signal to an input stage of a pulse generator 30a. If defibrillating therapy is to be applied, the signal from the control logic 29 may be encoded to identify the polarity of the high energy pulse. In systems using more than two electrodes, such as a transvenous lead with two patch electrodes, the polarity configuration of the shock delivery may be modified to deliver the pulse to the primary site of the disarrhythmia.

Figure 9:
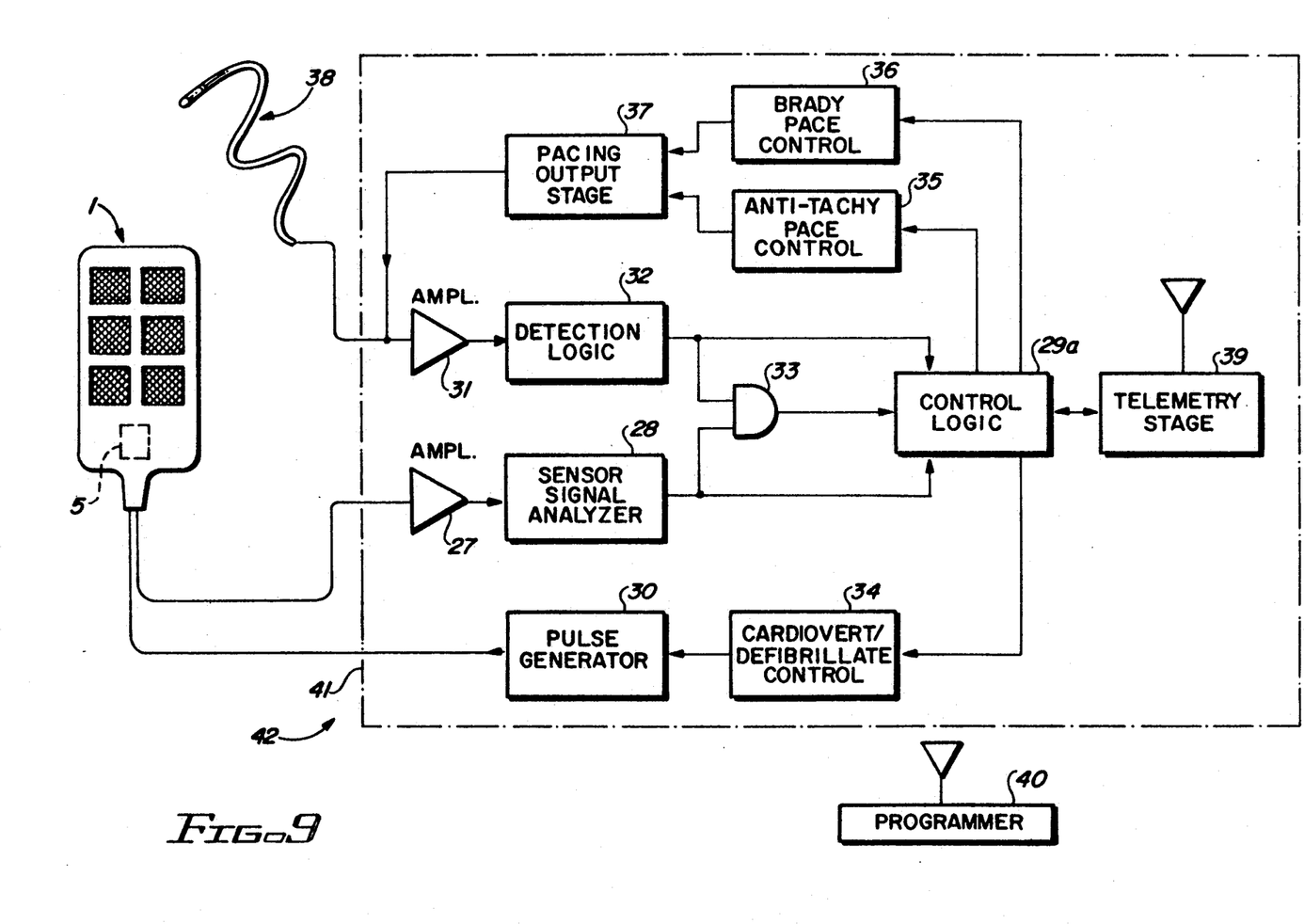
FIG. 9 is a schematic block diagram of an implantable pacing and defibrillating system constructed in accordance with the principles of the present invention.

A tachyarrhythmia control system 42 is shown in FIG. 9 which provides both defibrillation therapy and cardiac pacing assistance in a single implantable system. The system includes a patch electrode 1 having a motion sensor 5 embedded therein electrically connected to components in an implantable housing 41, and a conventional pacing lead 38, also electrically connected to components in the housing 41. The lead 38 may be a standard bipolar pacing/sensing lead. The second high energy shock lead could be a second patch electrode (not shown), or a transvenous electrode (not shown which could be mounted on the pacing lead 38). The signal from the motion sensor 5 is again supplied to an amplifier 27 and is analyzed in a sensor signal analyzer 28 as described above. The cardiac activity sensed by the pacing lead 38, such as R-waves, is supplied in a known manner via an amplifier 31 to conventional detection logic 32.

The respective outputs of the sensor signal analyzer 28 and the detection logic 32 are directly supplied to control logic 29a as separate signals, but are also logically combined in a gate 33, such as an AND gate, the output of which is also supplied to the control logic 29a. The control logic may assume any one of a number of modes or states by virtue of being telemetrically programmed by an external programmer 40 via a telemetry stage 39 contained within the implantable housing 41 and electrically connected to the control logic 29a. The telemetry system may also be used, via the control logic 29a, to program any of the other components within the implantable housing 41, and for this purpose the logic 29a may be provided with storage capacity, or a separate memory may be provided.

The control logic 29a may be programmed to make use of only the signal from the detection logic 32, only the signal from the sensor signal analyzer 28, the combined signal from the logic gate 33, or combinations thereof. The signal from the sensor signal analyzer 28 may thus not only be used as a primary or secondary indicator of the onset of fibrillation, but may also be used as a primary or secondary indicator of less severe arrhythmia, such as the onset of tachycardia.

The detection logic 32 may be used in a standard manner as providing data for standard bradycardia pacing support, in which case the control logic 29a will enable a bradycardia pacing control unit 36 for generating standard pacing pulses via a pacing output stage 37, delivered the lead 38. This may be accomplished in any of the known pacing modes. When the onset of tachycardia is identified either by the detection logic 32 alone, the sensor signal analyzer 28 alone, or a combination of the respective signals therefrom, the control logic 29a enables an antitachycardia pacing control stage 35, which causes pacing pulses to be generated by the pacing output stage 37 in a sequence calculated to terminate the tachycardia using any of the known pulse sequencing techniques for this purpose. Alternately, control logic 29a could enable a cardiovert/defibrillator control stage 34 which would cause a low energy cardioversion. When the onset of fibrillation is detected, the control logic 29a enables the cardiovert/defibrillate control stage 34 which causes a high energy defibrillation pulse to generated by the pulse generator 30 via the patch electrode 1.

Figure 10:
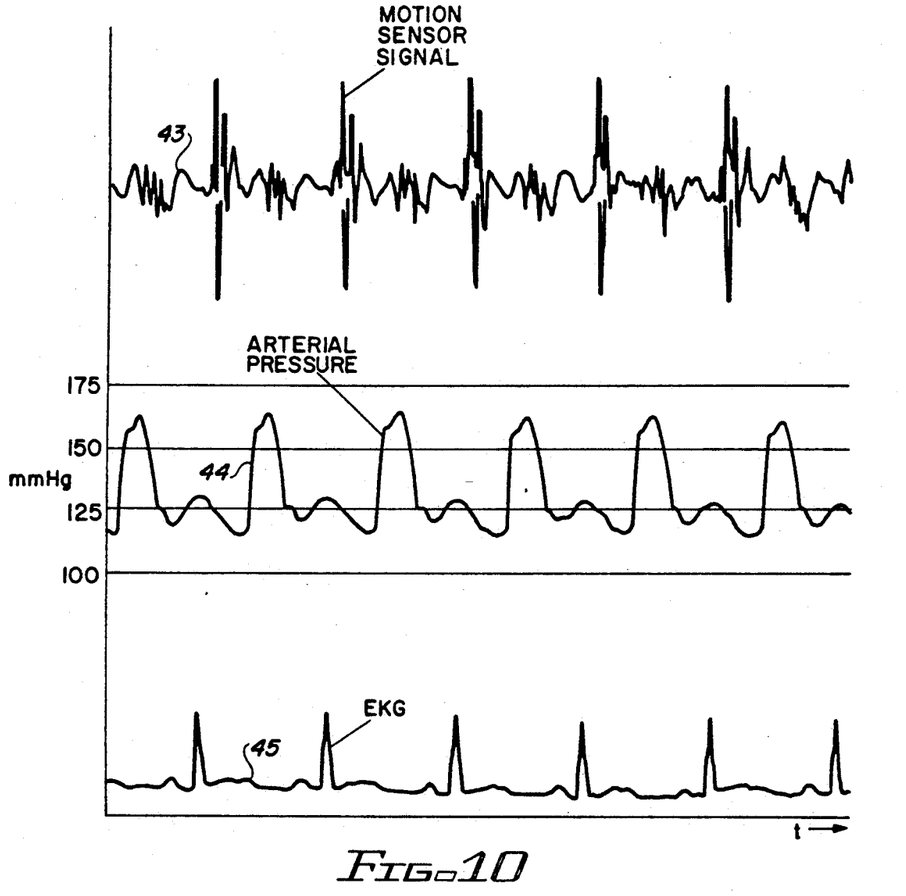
FIG. 10 is a graph showing the piezoelectric sensor signal, the aortic pressure signal, and a surface EKG signal for explaining the operation of the tachyarrhythmia control system disclosed herein.

A standard or base line signal 43 from the motion sensor 5 as occurs during "normal" cardiac activity is shown at the top of FIG. 10. For reference purposes, this signal is shown on the same time scale with an arterial pressure signal 44 and a surface EKG signal 45. Note that the arterial pressure signal 44 is delayed somewhat due to the location of the pressure sensor; the large pressure spike in fact closely follows the QRS complex.

As can be seen in FIG. 10, during normal cardiac activity the motion sensor signal 43 exhibits a regular periodicity, and a relatively low frequency and amplitude. Upon the onset of tachycardia, it has been observed that the frequency and amplitude of the signal 43 significantly increase, the amplitude in particular doubling or tripling. Upon the onset of ventricular fibrillation, the increase in amplitude becomes even more dramatic, approximately four to five times the amplitude of the normal signal shown in FIG. 10. Since the amplitude and frequency of the signal 43 in combination determine the "energy content" (proportional to the area under the curve) of the signal 43, any one or a combination of the amplitude, frequency or energy content of the signal 43 can be used as a reliable indicator for the onset of these types of cardiac activity.

Although modifications and changes may be suggested by those skilled in the art, it is the intention of the inventor to embody within the patent warranted hereon all changes and modifications as reasonably and properly come within the scope of his contribution to the art.

What is claimed is:

1. An implantable tachyarrhythmia control system comprising:
   a flexible patch electrode adapted to be attached in vivo to cardiac tissue of a patient, said patch electrode including means for stimulating said cardiac tissue and having a motion sensor means embedded therein for generating an electrical signal corresponding to cardiac wall movement;
   means adapted for in vivo electrical connection to said motion sensor means for analyzing said electrical signals to identify the presence of tachycardia;
   means adapted for in vivo electrical connection to said means for stimulating, and electrically connected to said means for analyzing, for initiating therapeutic electrical treatment via said means for stimulating cardiac tissue upon the identification of tachyarrhythmia by said means for analyzing; and
   a housing containing said means for analyzing and said means for initiating therapeutic electrical treatment adapted for implantation in said patient.

2. An implantable tachyarrhythmia control system as claimed in claim 1 wherein said motion sensor means is a piezoelectric sensor.

3. An implantable tachyarrhythmia control system as claimed in claim 1 wherein said means for analyzing is a means for detecting the onset of fibrillation, wherein said means for initiating therapeutic electrical treatment is a means for generating electrical defibrillation therapy, and wherein said means for stimulating cardiac tissue is a means for delivering said defibrillating electrical therapy to said cardiac tissue.

4. An implantable tachyarrhythmia control system as claimed in claim 3 wherein said means for delivering defibrillating electrical therapy to said cardiac tissue is a wire mesh electrode contained in said patch electrode and adapted for direct contact with said cardiac tissue.

5. An implantable tachyarrhythmia control system as claimed in claim wherein said patch electrode further includes a cable containing electrical lines connecting said motion sensor means to said means for analyzing and said means for stimulating to said means for initiating therapeutic electrical treatment, and a carrier connected to said cable at terminal region of said carrier, said carrier having an electrode region in which said means for stimulating is disposed and a neck region, between said electrode region and said terminal region, in which said motion sensor means is disposed.

6. An implantable tachyarrhythmia control system as claimed in claim 1 further comprising:
   a further flexible patch electrode adapted to be attached in vivo to cardiac tissue in a patient, said further patch electrode including further means for stimulating said cardiac tissue and having a further motion sensor means embedded therein for generating an electrical signal corresponding to cardiac wall movement, said means for analyzing being adapted for in vivo electrical connection to said further motion sensor means and said means for initiating therapeutic electrical treatment being adapted for in vivo electrical connection to said further means for stimulating cardiac tissue.

7. An implantable tachyarrhythmia control system comprising:
a first flexible patch electrode adapted to be attached in vivo to cardiac tissue, said first patch electrode including first means for stimulating said cardiac tissue and having a first motion sensor means embedded therein for generating a first electrical signal corresponding to cardiac wall movement;
a second flexible patch electrode adapted to be attached in vivo to said cardiac tissue, said second patch electrode including second means for stimulating said cardiac tissue and having a second motion sensor means embedded therein for generating a second electrical signal corresponding to cardiac wall movement;
means adapted for electrical connection in vivo to said first and second motion sensor means for analyzing said first and second electrical signals to identify the presence of tachyarrhythmia and for identifying which of said first or second electrical signals indicates the presence of tachycardia;
means adapted for in vivo electrical connection to said first and second means for stimulating, and electrically connected to said means for analyzing, for initiating therapeutic electrical treatment via one or both of said means for stimulating cardiac tissue upon the identification of tachycardia dependent upon which of said first or second electrical signals indicate the presence of tachycardia; and
a housing adapted for implantation in said patient and containing said means for analyzing and said means for initiating therapeutic electrical treatment.

8. An implantable tachyarrhythmia control system as claimed in claim 7 wherein each of said first and second motion sensor means is a piezoelectric sensor.

9. An implantable tachyarrhythmia control system as claimed in claim 7 wherein said means for analyzing is a means for detecting the presence of fibrillation, wherein said means for initiating therapeutic electrical treatment is a means for initiating electrical defibrillation therapy, and wherein said first and second means for stimulating are each means for delivering said electrical defibrillation therapy to said cardiac tissue.

10. An implantable tachyarrhythmia control system comprising:
means adapted to be attached in vivo to cardiac tissue for mechanical interaction with said cardiac tissue for generating a first electrical signal corresponding to mechanical cardiac activity;
means adapted to be placed in contact in vivo with said cardiac tissue for electrical interaction with said cardiac tissue for generating a second electrical signal corresponding to electrical cardiac activity;
means adapted for in vivo electrical connection to said means for mechanical interaction with said cardiac tissue for analyzing said first electrical signal to identify the presence of tachyarrhythmia;
means adapted for in vivo electrical connection to said means for electrical interaction with said cardiac tissue for analyzing said second electrical signal to identify the presence of tachyarrhythmia;
means adapted for in vivo contact with said cardiac tissue for electrically stimulating said cardiac tissue;
means adapted for in vivo connection to said means for stimulating, and electrically connected to each of said means for analyzing said first and second electrical signals, for initiating therapeutic electrical treatment via said means for stimulating cardiac tissue upon the identification of tachyarrhythmia; and
a housing adapted for implantation in said patient and containing said means for analyzing said first electrical signal, said means for analyzing said second electrical signal, and said means for initiating therapeutic electrical treatment.

11. An implantable tachyarrhythmia control system as claimed in claim 10 wherein said means for analyzing said first electrical signal is a means for analyzing said first electrical signal for identifying the presence and type of tachycardia, wherein said means for analyzing said second electrical signal is a means for analyzing second electrical signal to identify the presence and the type of tachycardia, wherein said means for stimulating said cardiac tissue includes means adapted for delivering high energy therapeutic electrical treatment to said cardiac tissue and means adapted for delivering low energy therapeutic electrical treatment to said cardiac tissue and wherein said means for initiating therapeutic electrical treatment upon the identification of tachycardia includes means for selecting high or low energy therapeutic electrical treatment dependent on the type of tachycardia identified by each of said means for analyzing said first and second electrical signals.

12. An implantable tachyarrhythmia control system as claimed in claim 11 wherein said means adapted for delivering high energy therapeutic electrical treatment to said cardiac tissue is a defibrillator patch electrode, and wherein said means for mechanical interaction with said cardiac tissue is mounted in said patch electrode.

13. An implantable tachyarrhythmia control system as claimed in claim 11 wherein said means adapted for mechanical interaction with said cardiac tissue is a piezoelectric sensor adapted for placement relative to said cardiac tissue for detecting cardiac wall movement.

14. An implantable tachyarrhythmia control system comprising:
a flexible patch electrode adapted to be attached in vivo to cardiac tissue of a patient, said electrode including means for stimulating said cardiac tissue with defibrillating electrical therapy and first sensor means adapted for mechanical interaction with said cardiac tissue for generating a first signal indicative of mechanical cardiac activity;
a pacing lead including means for stimulating said cardiac tissue with pacemaking electrical therapy and second sensor means adapted for electrical interaction with said cardiac tissue for generating a second signal indicative of electrical cardiac activity;
first therapy means adapted for in vivo electrical connection to said means for stimulating in said pacing lead for generating electrical pacing pulses in an antitachycardia sequence;
second therapy means adapted for in vivo electrical connection to said means for stimulating in said patch electrode for generating electrical cardioversion or defibrillating pulses;

first logic means adapted for in vivo electrical connection to said first sensor means for analyzing said first signal to identify, in an output signal of said first logic means, the presence of tachycardia or fibrillation;

second logic means adapted for in vivo electrical connection to said second sensor means for analyzing said second signal to identify, in an output signal of said second logic means, at least the presence of tachycardia;

means for logically combining the respective output signals of said first and second logic means;

control logic means to which the respective output signals of each of said first and second logic means and said means for logically combining are supplied, and connected to said first and second therapy means, for initiating an electrical therapy by enabling one of said first or second therapy means dependent on whether said output signals indicate the presence of tachycardia or fibrillation;

a housing adapted for implantation in said patient containing said first and second therapy means, said first and second logic means, said means for logically combining, and said control logic means.

15. An implantable tachyarrhythmia control system as claimed in claim 14 further comprising:

third therapy means, contained in said housing and adapted for in vivo electrical connection to said means for stimulating in said pacing lead, for generating pacemaking pulses in a sequence for treatment of bradycardia, said third therapy means being connected to said control logic means and being enabled by said control logic means in the absence of tachycardia or fibrillation.

16. An implantable tachyarrhythmia control system as claimed in claim 14 further comprising:

means for telemetrically programming said control logic means for selecting any one, or any combination, of said output signals of said first and second logic means and said means for logically combining as the basis for initiating said electrical therapy.

17. An implantable tachyarrhythmia control system as claimed in claim 14 wherein said means for logically combining is an AND gate.

18. An implantable tachyarrhythmia control system as claimed in claim 14 wherein said second logic means is an R-wave detection circuit.

19. An implantable tachyarrhythmia control system as claimed in claim 14 wherein said means for mechanically interacting with said cardiac tissue is a piezoelectric sensor.

20. A defibrillator patch electrode comprising:

means adapted for in vivo contact with cardiac tissue for delivering defibrillating electrical energy to said cardiac tissue; and means adapted for mechanically interacting with said cardiac tissue for generating an electrical signal corresponding to mechanical activity of said cardiac tissue.

21. A patch electrode as claimed in claim 20 wherein said means for mechanically interacting with said cardiac tissue is a piezoelectric sensor.

22. A patch electrode as claimed in claim 21 wherein said piezoelectric sensor comprises:

a metallic backing; and a piezoelectric crystal attached to said metallic backing.

23. A patch electrode as claimed in claim 22 wherein said metallic backing consists of titanium.

24. A defibrillating patch electrode comprising:

a carrier having an electrode region, a terminal region adapted for mechanical and electrical connection to an electrical cable, and a neck region disposed between said electrode region and said terminal region;

means disposed in said electrode region adapted for in vivo contact with cardiac tissue for delivering defibrillating electrical energy to said cardiac tissue; and means disposed in said neck region for mechanically interacting with said cardiac tissue for generating an electrical signal corresponding to mechanical activity of said cardiac tissue.

25. A patch electrode as claimed in claim 24 wherein said means for mechanically interacting with said cardiac tissue is a piezoelectric sensor.

26. A patch electrode as claimed in claim 24 wherein said electrode region has a figure-eight shape formed by two lobes joined by a narrow region, and wherein said neck region is disposed at a side of one of said lobes closest to said narrow region.

27. A patch electrode as claimed in claim 24 wherein said electrode region has a figure-eight shape formed by two lobes joined by a narrow region, and wherein said neck region is disposed at a side of one of said lobes farthest from said narrow region.

28. A patch electrode as claimed in claim 24 wherein said electrode region has a rabbit ear shape formed by two lobes with a narrow region therebetween, and wherein said neck region of said carrier is adjacent said narrow region.

29. A patch electrode as claimed in claim 24 wherein said electrode region is triangular, and wherein said neck region is disposed at an apex of said electrode region.

30. A patch electrode as claimed in claim 29 wherein said electrode region is in the shape of an isosceles triangle, and wherein said neck region is disposed at an apex of said isosceles triangle at which sides of equal length meet.

31. A patch electrode as claimed in claim 24 further comprising:

first and second electrical leads for said means for mechanically interacting with said cardiac tissue;

a third electrical lead for said means for delivering defibrillating electrical energy; and a cable extending from said carrier and containing all of said first, second and third leads, said cable terminating in a first branch containing said first and second leads and a terminal assembly therefor, and a second branch containing only said third lead and a terminal assembly therefor.

32. A patch electrode as claimed in claim 24 further comprising:

first and second electrical leads for said means for mechanically interacting with said cardiac tissue;

a third electrical lead for said means for delivering defibrillating electrical energy, said first lead being electrically connected in said carrier to said third lead; and a cable extending from said carrier containing said second and third leads and terminating in a single terminal assembly.

33. A patch electrode as claimed in claim 24 wherein said carrier has a surface thereof adapted for in vivo contact with said cardiac tissue, and wherein said means for mechanically interacting with said cardiac tissue is disposed adjacent said surface.

34. A patch electrode as claimed in claim 24 wherein said carrier has a surface adapted to face away in vivo from said cardiac tissue, and wherein said means for mechanically interacting with said cardiac tissue is disposed adjacent said surface.

35. A method for treating fibrillation in a patient comprising the steps of:
   attaching a defibrillator patch electrode to cardiac tissue;
   mounting a sensor in said patch electrode for detecting mechanical activity of said cardiac tissue and generating an electrical signal corresponding to said mechanical activity;
   monitoring said electrical signal to identify characteristics of said electrical signal indicating the presence of fibrillation; and
   undertaking defibrillation therapy by applying electrical energy to said cardiac tissue via said patch electrode when said characteristics indicating fibrillation are present in said electrical signal.

36. A method as claimed in claim 35 wherein said electrical signal also includes characteristics indicating the presence of tachycardia, and comprising the additional steps of:
   placing a pacing electrode in contact with said cardiac tissue for delivery of pacemaking pulses to said cardiac tissue;
   monitoring said electrical signal to identify said characteristics therein indicating the presence of tachycardia; and
   initiating an antitachycardia pacing sequence via said pacing electrode upon the identification of said characteristics in said electrical signal indicating tachycardia.

37. A method as claimed in claim 36 comprising the additional step of:
   administering a bradycardia pacing sequence to said cardiac tissue via said pacing electrode in the absence of characteristics in said electrical signal indicating tachycardia or fibrillation.

* * * * *

UNITED STATES PATENT AND TRADEMARK OFFICE
CERTIFICATE OF CORRECTION

PATENT NO. : 5,109,842
DATED : May 5, 1992
INVENTOR(S) : David W. Adinolfi

It is certified that error appears in the above-indentified patent and that said Letters Patent is hereby corrected as shown below:

In col. 8, line 49, delete "as claimed in claim wherein" and insert therefor --as claimed in claim 1 wherein--.

Signed and Sealed this

Twenty-third Day of May, 1995

Attest:

BRUCE LEHMAN

Attesting Officer  Commissioner of Patents and Trademarks